(12) United States Patent
Kuebel

(10) Patent No.: US 8,402,808 B2
(45) Date of Patent: Mar. 26, 2013

(54) FUNCTION TEST OF FUEL CELL EXHAUST GAS STREAM HYDROGEN SENSOR BY GENERATING DEFINED HYDROGEN PULSES WHILE DRIVING AND AT REGULAR SERVICE WITH FUEL CELL SYSTEM IMMANENT DEVICES

(75) Inventor: Christoph Kuebel, Wiesbaden (DE)

(73) Assignee: GM Global Technology Operations LLC, Detroit, MI (US)

( * ) Notice: Subject to any disclaimer, the term of this patent is extended or adjusted under 35 U.S.C. 154(b) by 307 days.

(21) Appl. No.: 12/797,444

(22) Filed: Jun. 9, 2010

(65) Prior Publication Data

US 2011/0302993 A1 Dec. 15, 2011

(51) Int. Cl.
*G01N 33/00* (2006.01)
(52) U.S. Cl. ......................................... 73/1.03
(58) Field of Classification Search ............... 73/1.03, 73/1.06
See application file for complete search history.

(56) References Cited

U.S. PATENT DOCUMENTS

| | | | | |
|---|---|---|---|---|
| 2003/0187567 | A1* | 10/2003 | Sulatisky et al. | 701/104 |
| 2004/0197621 | A1* | 10/2004 | Balliet et al. | 429/22 |
| 2005/0058861 | A1* | 3/2005 | Pettit et al. | 429/22 |
| 2008/0118423 | A1* | 5/2008 | Fattic et al. | 423/235 |

FOREIGN PATENT DOCUMENTS

JP 2006252933 A * 9/2006

* cited by examiner

*Primary Examiner* — Hezron E Williams
*Assistant Examiner* — Nashmiya Fayyaz
(74) *Attorney, Agent, or Firm* — John A. Miller; Miller IP Group, PLC

(57) ABSTRACT

A system and method for determining whether a hydrogen concentration sensor in the exhaust of a fuel cell system is operating properly during operation of the system. The method includes injecting hydrogen gas pulses from an injector directly into the system exhaust and analyzing a sensor response from those hydrogen injection pulses. Alternately, pulses from anode purges or bleeds can be provided to the exhaust to determine sensor response.

20 Claims, 1 Drawing Sheet

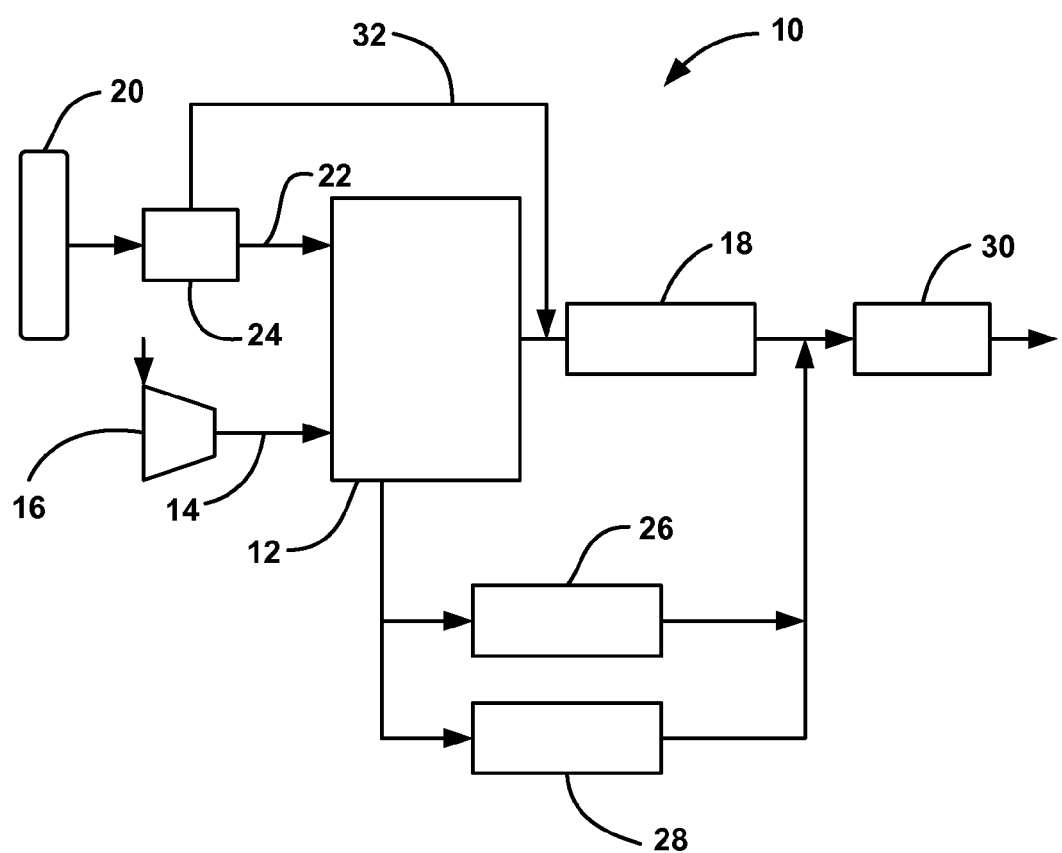

ure and method for providing hydrogen pulses during fuel cell system operation to test a hydrogen concentration sensor in the system exhaust and, more particularly, to a system and method for providing fixed gas pulses from a hydrogen injector, an anode purge valve and/or an anode bleed valve directly to a system exhaust to test a hydrogen concentration sensor in the exhaust.

FUNCTION TEST OF FUEL CELL EXHAUST GAS STREAM HYDROGEN SENSOR BY GENERATING DEFINED HYDROGEN PULSES WHILE DRIVING AND AT REGULAR SERVICE WITH FUEL CELL SYSTEM IMMANENT DEVICES

BACKGROUND OF THE INVENTION

1. Field of the Invention

This invention relates generally to a system and method for providing hydrogen pulses during fuel cell system operation to test a hydrogen concentration sensor in the system exhaust and, more particularly, to a system and method for providing fixed gas pulses from a hydrogen injector, an anode purge valve and/or an anode bleed valve directly to a system exhaust to test a hydrogen concentration sensor in the exhaust.

2. Discussion of the Related Art

Hydrogen is a very attractive fuel because it is clean and can be used to efficiently produce electricity in a fuel cell. A hydrogen fuel cell is an electro-chemical device that includes an anode and a cathode with an electrolyte there between. The anode receives hydrogen gas and the cathode receives oxygen or air. The hydrogen gas is dissociated at the anode catalyst to generate free protons and electrons. The protons pass through the electrolyte to the cathode. The protons react with the oxygen and the electrons at the cathode catalyst to generate water. The electrons from the anode cannot pass through the electrolyte, and thus are directed through a load to perform work before being sent to the cathode.

Proton exchange membrane fuel cells (PEMFC) are a popular fuel cell for vehicles. The PEMFC generally includes a solid polymer electrolyte proton conducting membrane, such as a perfluorosulfonic acid membrane. The anode and cathode electrodes, or catalyst layers, typically include finely divided catalytic particles, usually platinum (Pt), supported on carbon particles and mixed with an ionomer. The catalytic mixture is deposited on opposing sides of the membrane. The combination of the anode catalytic mixture, the cathode catalytic mixture and the membrane define a membrane electrode assembly (MEA). Each MEA is usually sandwiched between two sheets of porous material, the gas diffusion layer (GDL), that protects the mechanical integrity of the membrane and also helps in uniform reactant humidity diffusion. MEAs are relatively expensive to manufacture and require certain conditions for effective operation.

Several fuel cells are typically combined in a fuel cell stack to generate the desired power. For example, a typical fuel cell stack for a vehicle may have two hundred or more stacked fuel cells. The fuel cell stack receives a cathode reactant input gas, typically a flow of air forced through the stack by a compressor. Not all of the oxygen is consumed by the stack and some of the air is output as a cathode exhaust gas that may include water as a stack by-product. The fuel cell stack also receives an anode hydrogen reactant input gas that flows into the anode side of the stack.

A fuel cell stack typically includes a series of bipolar plates positioned between the several MEAs in the stack, where the bipolar plates and the MEAs are positioned between two end plates. The bipolar plates include an anode side and a cathode side for adjacent fuel cells in the stack. Anode gas flow fields are provided on the anode side of the bipolar plates that allow the anode reactant gas to flow to the respective MEA. Cathode gas flow fields are provided on the cathode side of the bipolar plates that allow the cathode reactant gas to flow to the respective MEA. One end plate includes anode gas flow channels, and the other end plate includes cathode gas flow channels.

The bipolar plates and end plates are made of a conductive material, such as stainless steel or a conductive composite. The end plates conduct the electricity generated by the fuel cells out of the stack. The bipolar plates also include flow channels through which a cooling fluid flows.

Many fuel cells systems for vehicles employ hydrogen concentration sensors in the system exhaust for safety purposes to monitor and prevent hydrogen emissions above a certain concentration. In one known system, a complex and expensive hydrogen concentration sensor is employed that includes two sensing chips and two CPUs. This type of sensor needs to have a functionality and calibration test performed at regular intervals, such as every three months, with a premixed test gas at an approved service center. Further, these sensors would also need to be calibrated and tested at normal maintenance events for the vehicle. Thus, in order to effectively monitor hydrogen gas emissions from a fuel cell vehicle, an expensive sensor would be required, expensive test equipment would be required and premixed gases would be required at a service center, all adding significant cost to the vehicle.

SUMMARY OF THE INVENTION

In accordance with the teachings of the present invention, a system and method are disclosed for determining whether a hydrogen concentration sensor in the exhaust of a fuel cell system is operating properly during operation of the system. The method includes injecting hydrogen gas pulses from an injector directly into the system exhaust and analyzing a sensor response from those hydrogen injection pulses. Alternately, pulses from anode purges or bleeds can be provided to the exhaust to determine sensor response.

Additional features of the present invention will become apparent from the following description and appended claims, taken in conjunction with the accompanying drawings.

BRIEF DESCRIPTION OF THE DRAWING

FIG. 1 is a block plan view of a fuel cell system.

DETAILED DESCRIPTION OF THE EMBODIMENTS

The following discussion of the embodiments of the invention directed to a system and method for testing a hydrogen concentration sensor in the exhaust of a fuel cell system during system operation is merely exemplary in nature, and is in no way intended to limit the invention or its applications or uses.

FIG. 1 is a block plan view of a fuel cell system 10 including a fuel cell stack 12. The fuel cell stack 12 is intended to represent a number of combined components in a fuel cell power system for a vehicle, including multiple sub-stacks for an anode flow-shifting type fuel cell system. The cathode side of the fuel cell stack 12 receives an airflow on a cathode input line 14 from a compressor 16 and a system exhaust gas is output from the stack 12 through an exhaust pipe 18. Hydrogen gas from a hydrogen tank 20 is injected into the anode side of the fuel cell stack 12 on an anode input line 22 by a bank of injectors 24.

A purge valve 26 is provided to purge the anode side of fuel cell stack 12 in a controlled manner to remove gas quickly from the anode of the stack 12 and a bleed valve 28 is provided to bleed nitrogen from the anode side of the fuel cell stack 12 at predetermined intervals in a manner that is well understood to those skilled in the art. Typical fuel cell systems, including anode flow-shifting type fuel cell systems, employ purge valves to purge the anode side of the fuel cell stack at certain times, such as at shut-down, with air to remove remaining hydrogen and water in the flow channels for freeze situations and therefore providing other benefits. Further, because MEAs are porous, nitrogen in the air from the cathode side of the stack permeates through the membranes and collects in the anode side, known as nitrogen cross-over. Nitrogen in the anode side of the fuel cell stack dilutes the hydrogen so that if the nitrogen concentration increases above a certain percentage, the fuel cell stack may become unstable. Thus, periodic leads of the anode side are necessary.

In the design shown for the system 10, the purged and bled anode gas is sent to the exhaust of the system 10 and is mixed with the air from the cathode side in the exhaust pipe 18. However, in other designs, the purged and bled anode gas can be sent to the cathode input on line 14 to generate water within the stack 12. A hydrogen concentration sensor 30 measures the concentration of hydrogen gas in the exhaust pipe 18 consistent with the discussion below.

The present invention proposes using hydrogen sources in the system 10 to provide hydrogen pulses that can be detected by the hydrogen sensor 30 to determine whether the sensor 30 is operating properly at various intervals during operation of the vehicle. In one example, one of the injectors in the bank of injector 24 is selected to direct a pulse of hydrogen gas around the stack 12 on line 32 directly to the exhaust pipe 18. Therefore, a pulse of a known quantity of hydrogen gas will be provided within the system exhaust, which can be detected by the sensor 30 and be analyzed to determine whether that concentration of hydrogen as mixed with the other gases in the exhaust is accurately detected.

The algorithms that would be employed to select the pulse duration and time from the injector would consider a number of system parameters, including various pressures, temperatures, compressor speed, power requirements, etc., so that the amount of hydrogen gas in the exhaust is at a level below the emissions requirements. Thus, the algorithm would look for the proper increase in the hydrogen gas concentration in the exhaust as a result of the controlled pulse providing a known amount of hydrogen to determine whether the sensor 30 is operating properly. In those situations where the vehicle is at a service center, a well defined hydrogen pulse could be produced by directing hydrogen gas into the exhaust when the fuel cell system is running at idle. This pulse could be just as high as specified to trigger the vehicle hydrogen alarm. In case of sensor malfunction, i.e. under or over prediction, the vehicle hydrogen alarm will not be triggered at all or will be trigger early.

As mentioned above, in a design for the system 10, the purge valve 26 and the bleed valve 28 caused the purged and bled anode gas to be directed to the exhaust pipe 18. During the purge and bleed event, the hydrogen sensor 30 would record an increase in the hydrogen concentration in the system exhaust as a result of the concentration of additional hydrogen being purged or bled from the stack 12. However, the length of the purge or bleed and the timing of that purge or bleed may or may not be ideal for determining the quality of the operation of the sensor 30. In an alternate design, the purged or bled anode gas may be sent to the cathode input on the line 14, and additional plumbing and valves can be provide to direct some of the purged and bled anode gas to the exhaust pipe 18 in a pulsed manner. In this manner, during a purge event, a selected and controlled amount of the anode gas could be directed to the exhaust for a controlled amount of time which could provide better results for analyzing the operation of the hydrogen sensor 30.

Therefore, less expensive sensors can be used for the hydrogen sensor 30 that require less sensing chips and less CPUs and reduce significantly the sensor requirements and sensor complexity. Further, the time interval between sensor service intervals can be increased.

The foregoing discussion disclosed and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A method for testing a hydrogen concentration sensor positioned in an exhaust gas line of a fuel cell system, said method comprising:
   providing a flow of exhaust gas from a fuel cell stack to the exhaust gas line;
   injecting a hydrogen gas from a hydrogen source to an anode side of the fuel cell stack using a plurality of injectors;
   using at least one of the injectors to inject a known quantity of hydrogen gas from the hydrogen source directly to the exhaust line in a pulsed manner; and
   detecting the pulse of hydrogen gas injected into the exhaust gas line by the hydrogen sensor and comparing the detected hydrogen gas by the hydrogen sensor to the known quantity of hydrogen gas to determine whether the hydrogen sensor is operating properly, wherein a pulse duration and time that the hydrogen gas is injected into the exhaust line is determined based on fuel cell system parameters based on algorithms such that the amount of hydrogen gas in the exhaust is approximately at or below a quantity specified to trigger a vehicle hydrogen alarm.

2. The method according to claim 1 further comprising providing a pulse of anode exhaust gas from the fuel cell stack to the exhaust gas line and detecting the pulse of anode exhaust gas by the hydrogen sensor to determine whether the hydrogen sensor is operating properly.

3. The method according to claim 2 wherein a remaining portion of the anode exhaust gas that is not part of the pulse of anode exhaust gas is provided to a cathode input of the fuel cell stack.

4. The method according to claim 2 wherein providing a pulse of anode exhaust gas includes providing a pulse of anode exhaust gas from a purge valve used to purge the anode side of the fuel cell stack.

5. The method according to claim 2 wherein providing a pulse of anode exhaust gas includes providing a pulse of anode exhaust gas from a bleed valve that is used to bleed the anode exhaust gas from the anode side of the fuel cell stack.

6. The method according to claim 1 wherein the fuel cell stack operates under anode flow-shifting.

7. A method for testing a hydrogen concentration sensor positioned in an exhaust line of a fuel cell system, said method comprising:
   providing a flow of exhaust gas from a fuel cell stack to the exhaust gas line;
   providing a pulse of anode exhaust gas with a known quantity of hydrogen gas from the fuel cell stack to the exhaust gas line from a component within the fuel cell system during normal operation of the fuel cell system; and detecting the pulse of anode exhaust gas with the known quantity of hydrogen gas by the hydrogen sensor and comparing a detected hydrogen gas by the hydrogen sensor to the known quantity of hydrogen gas to determine whether the hydrogen sensor is operating properly, wherein the pulse duration and time that the known quantity of hydrogen gas that is injected into the exhaust line is determined based on fuel cell system parameters based on algorithms such that the amount of hydrogen gas in the exhaust is approximately at or below a quantity specified to trigger a vehicle hydrogen alarm.

8. The method according to claim 7 further comprising providing a pulse of a known quantity of hydrogen gas directly from at least one injector that is otherwise used to inject hydrogen gas from a hydrogen source to an anode input of the fuel cell stack and detecting the direct pulse of the known quantity of hydrogen gas by the hydrogen sensor and comparing the detected hydrogen gas from the direct pulse to the known quantity of hydrogen gas to determine whether the hydrogen sensor is operating properly.

9. The method according to claim 7 wherein providing a pulse of anode exhaust gas includes providing a pulse of anode exhaust gas from a purge valve used to purge the anode side of the fuel cell stack.

10. The method according to claim 9 wherein a remaining portion of the anode exhaust gas that is not part of the pulse of anode exhaust gas is provided to a cathode input of the fuel cell stack.

11. The method according to claim 7 wherein providing a pulse of anode exhaust gas includes providing a pulse of anode exhaust gas from a bleed valve that is used to bleed the anode exhaust gas from the anode side of the fuel cell stack.

12. The method according to claim 11 wherein a remaining portion of the anode exhaust gas that is not part of the pulse of anode exhaust gas is provided to a cathode input of the fuel cell stack.

13. The method according to claim 7 wherein the fuel cell stack operates under anode flow-shifting.

14. A system for testing a hydrogen concentration sensor positioned in an exhaust line of a fuel cell system, said system comprising:

means for providing a flow of exhaust gas from a fuel cell stack to the exhaust gas line;

means for providing a pulse of anode exhaust gas with a known quantity of hydrogen gas from the fuel cell stack to the exhaust gas line from a component within the fuel cell system during normal operation of the fuel cell system; and means for detecting the pulse of anode exhaust gas with a known quantity of hydrogen gas by the hydrogen sensor and comparing a detected hydrogen gas by the hydrogen sensor to the known quantity of hydrogen gas to determine whether the hydrogen sensor is operating properly, wherein the pulse duration and time that the known quantity of hydrogen gas is injected into the exhaust line is determined based on fuel cell system parameters based on algorithms such that the amount of hydrogen gas in the exhaust is approximately at or below a quantity specified to trigger a vehicle hydrogen alarm.

15. The system according to claim 14 further comprising means for providing a pulse of hydrogen gas that provides a pulse of a known quantity hydrogen gas directly from at least one injector that is otherwise used to inject hydrogen gas from a hydrogen source to an anode input of the fuel cell stack and detecting the direct pulse of the known quantity of hydrogen gas by the hydrogen sensor and comparing the detected hydrogen gas from the direct pulse to the known quantity of hydrogen gas to determine whether the hydrogen sensor is operating properly.

16. The system according to claim 14 wherein the means for providing a pulse of anode exhaust gas provides a pulse of anode exhaust gas from a purge valve used to purge the anode side of the fuel cell stack.

17. The system according to claim 16 wherein a remaining portion of the anode exhaust gas that is not part of the pulse of anode exhaust gas is provided to a cathode input of the fuel cell stack.

18. The system according to claim 14 wherein the means for providing a pulse of anode exhaust gas provides a pulse of anode exhaust gas from a bleed valve that is used to bleed the anode exhaust gas from the anode side of the fuel cell stack.

19. The system according to claim 18 wherein a remaining portion of the anode exhaust gas that is not part of the pulse of anode exhaust gas is provided to a cathode input of the fuel cell stack.

20. The system according to claim 14 wherein the fuel cell stack operates under anode flow-shifting.

* * * * *